United States Patent [19]
Smith et al.

[11] Patent Number: 5,037,406
[45] Date of Patent: Aug. 6, 1991

[54] EYEDROP APPLICATOR ATTACHMENT

[76] Inventors: William L. Smith, P.O. Box 1334, Clayton, Ga. 30525; William E. Smith, 220 College St., Dyersburg, Tenn. 38027

[21] Appl. No.: 208,483

[22] Filed: Jun. 20, 1988

[51] Int. Cl.$^5$ ............................................. A61H 33/04
[52] U.S. Cl. .................................. 604/301; 222/568; 285/177
[58] Field of Search .............................. 604/294–302; 222/566, 570, 460, 461, 575; 141/367; 285/12, 175, 177; 215/319; 220/287; D24/66

[56] References Cited

U.S. PATENT DOCUMENTS

| | | | |
|---|---|---|---|
| D. 248,448 | 7/1978 | McClure et al. | D24/66 |
| 1,900,201 | 3/1933 | Sager | 604/296 |
| 2,080,268 | 5/1937 | Harris | 604/298 |
| 2,515,818 | 7/1950 | West | 604/301 |
| 2,585,264 | 2/1952 | Mock | 604/301 |
| 2,754,821 | 7/1956 | Burbig et al. | 604/298 |
| 3,016,898 | 1/1962 | Erwin | 604/301 |
| 3,279,466 | 10/1966 | Mings | 604/302 |
| 3,809,300 | 5/1974 | Russell | 222/562 |
| 3,945,381 | 3/1976 | Silver | 604/301 |
| 4,111,200 | 10/1978 | Sbarra et al. | 604/298 |
| 4,266,813 | 5/1981 | Oliver | 285/12 |
| 4,712,812 | 12/1985 | Weir III | 285/177 |
| 4,834,728 | 5/1989 | McKenna | 222/566 |

FOREIGN PATENT DOCUMENTS

| | | | |
|---|---|---|---|
| 1034498 | 7/1959 | Fed. Rep. of Germany | 222/570 |
| 0647481 | 10/1962 | Italy | 604/302 |
| 2142829 | 1/1985 | United Kingdom . | |

*Primary Examiner*—John D. Yasko
*Assistant Examiner*—Anthony Gutowski
*Attorney, Agent, or Firm*—Mason, Fenwick & Lawrence

[57] ABSTRACT

An eyedrop applicator attachment for attachment to a bottle having a large or small threaded neck. The applicator attachment is provided with a hollow cylindrical body, and an eyecup integral with the body at one end. The other end of the body has an opening, and interiorly of the body are two female threads, located coaxially and of different diameters, the threads with the larger diameter being adjacent the open end of the body. Thus, the applicator attachment may be attached to a squeeze bottle with a larger diameter neck, or to a squeeze bottle with a smaller diameter neck. In an alternate embodiment, axially of the threads for engagement with the neck of a bottle, there is an extension having a third female thread, into which a plug is threaded to provide a closure for the nozzle of a bottle attached to the cylindrical body.

In an alternate embodiment, the eyecup is intergral with the neck of a bottle, which may be of molded plastic, and provided with a snap fitting for receiving a nozzle insert, there being a cylindrical extension between the neck portion of the bottle and the eyecup which is internally threaded to receive a stopper which is in part hollow to receive and engage with a surface thereof the end of the drop-forming nozzle.

There are also provided an alternate embodiment in which a stopper and an attachment body have mating double threads, and the stopper has gripping means on the exterior or interior thereof. Further, a combined lid and stopper may be provided, with provision for relative sliding and rotatable movement.

4 Claims, 3 Drawing Sheets

EYEDROP APPLICATOR ATTACHMENT

BACKGROUND OF THE INVENTION

The present invention relates to an eyedrop applicator attachment for squeeze-type eyedrop bottles, and to an integral bottle and eyecup construction.

There have been provided various constructions of attachments for bottles for dispensing eyedrops which include an eyecup intended to hold open one or both of the eyelids, so as to enable drops which are dispensed from the squeeze-type bottle, or the like, and to enter into the eye. West U.S. Pat. No. 2,516,818 provides a medicinal applicator including an eyedrop dispensing nozzle, an eyecup, and a threaded cap for attachment to the neck of a bottle. Mock U.S. Pat. No. 2,585,264, Erwin U.S. Pat. No. 3,016,898, and Mings U.S. Pat. No. 3,279,446 provide generally similar constructions. In addition, McClure Design 248,448 provides an eyedrop applicator attachment for a squeeze bottle, and including a cap for the end of the eyecup. While these constructions have been generally effective in enabling the dispensing of eyedrops into the eye of the patient with minimum loss and with substantial effectiveness, there have been found to be problems in the commercially supplying eyecup attachments, and therefor the utilization of them.

Eyecup attachments are not generally provided with the conventional squeeze-bottle eyedrop container which has an attached drop dispensing nozzle. Thus, it is left to the purchaser to acquire from a separate source an eyecup attachment for attachment to the squeeze bottle for the eyedrops.

It has been discovered that there are a large number of producers of small plastic bottles for use as eyedrop dispensers, and that there have now been substantially standardized several different sizes of such bottles, designated in the trade as Size No. 13 and Size No. 15. The Size No. 13 is provided with threads on the neck of the bottle having an outer diameter of approximately 13 mm; the Size No. 15 bottle is provided with threads on the neck having an outer diameter just slightly smaller than 15 mm. In addition, it is now the universal practice for bottles of medication to be produced with some form of tamper-proof construction, and in some cases this is an outstanding bead at the end of the neck, to accommodate and to cooperate with a tamper-proofing seal. It has been determined that the outside diameter of such beads on the Size No. 13 bottles is not always small enough to fit inside the conventional closure cap for the Size No. 15 bottle.

Substantially all of the known above noted Size No. 13 and Size No. 15 bottles have the same pitch threads, which is 0.083 threads per inch. It has been found, additionally, that the distance from the end of the thread of the bottle which is at the distal end of the neck to the end of the bottle, and to the shoulder on an inserted dropper nozzle is a dimension which varies from 0.03 to 00.1 inches. Another important aspect of the eyedrop applicator bottles now being marketed is the distance from the noted tamper-proof seal to the above noted shoulder on the nozzle, which on the Size No. 13 bottles is 0.35 inches. The foregoing factors necessarily enter into the construction of any eyedropper attachment which can be attached to substantially all of the various eyedropper bottles now being sold.

SUMMARY OF THE INVENTION

There is provided an eyedrop applicator attachment having a cylindrical body with an open end, with a relatively large diameter female thread adjacent the open end, and with a smaller female thread inwardly of the first noted thread. The axial length of the portion of the body having the larger thread is small, so as to engage approximately one turn of the thread on a bottle having a larger diameter neck; consequently a bottle of smaller diameter neck may be inserted into the body and engage the smaller threads, without interference between the shoulder of the bottle and the attachment which would prevent their engagement. An eyecup is integral with and extends from the opposite end of the body: either a bottle having relatively larger or relatively smaller threads may have the attachment screw threadedly attached to it.

In an alternate embodiment, the cylindrical body of the attachment is somewhat extended at the end opposite the above noted open end, and has a female thread, to which a threaded stopper may be joined, the stopper engaging an extending drop-forming nozzle of an eyedrop dispensing bottle to seal it. The male thread of the stopper and the female thread of the cylindrical body engaged by the stopper may be double threads, for greater security of engagement between these parts.

There is also disclosed a bottle and eyecup which are integrally formed, with a nozzle insert for snap-fitting engagement into the mouth of the bottle: an axial extension is between the neck of the bottle and the eyecup, having female thread, to which a hollow stopper may be joined, the hollow stopper having a surface for engaging and closing off the orifice of the nozzle.

The stopper may be provided with knurling on the outside for facilitating turning by the fingers, or be of thimbleshape, with an interior protrusion, for the same purpose, or may have both of these constructions.

Another embodiment of an eyedrop applicator attachment includes a cylindrical body having the above noted first and second threads of different sizes for engaging different size eyedrop bottles, a third thread in which a stopper is engaged, the stopper being within an eyecup extending from the cylindrical body, and a lid or cap which engages the edge of the eyecup in a snap-fit, the lid having a central opening receiving the stopper for axial and rotatable movement relative to the lid.

Among the objects of the present invention are the provision of an eyedrop applicator attachment capable of being used with substantially all of the eyedropper bottles now being produced.

Another object is to provide an eyedrop applicator attachment having serially arranged internal threads of different size, with the larger size adjacent the open end of the attachment, for receiving bottles of different sizes.

Yet another object is the provision of an eyedrop applicator attachment capable of attachment to substantially any of the eyedrop applicator bottles now being produced, and which is provided with a closure stopper for the bottle.

Yet another object of the present invention is to provide a combined eyedrop dispenser bottle, eyecup and stopper.

Other objects and many of the attendant advantages of the present invention will be readily understood from the following specification, claims and drawings.

DESCRIPTION OF THE PREFERRED EMBODIMENTS

Figure 1:
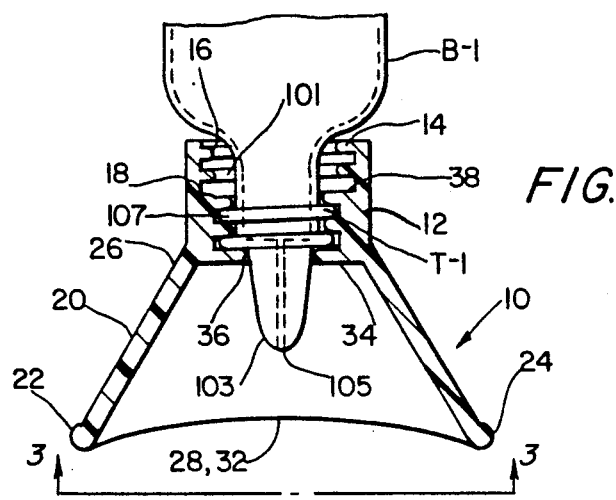
FIG. 1 is a cross-sectional view of an eyedrop applicator attachment in accordance with the present invention, and having a standard bottle of small diameter neck attached to it.

Referring now to the drawings, wherein like or corresponding reference numerals are used for like or corresponding parts throughout the several views, there is shown in FIG. 1 an eyedrop applicator 10, preferably of material which is impact resistant, such as soft polypropylene, which includes a hollow cylindrical body 12 having an open outer end 14. Adjacent the open outer end 14 is a female thread 16 of relatively large diameter Also on the interior of the hollow cylindrical body 12 is a second female thread 18 which is of smaller diameter than the first female thread 16. As shown, the second female thread 18 is on the interior of the hollow cylindrical body 12 axially of the first female thread 16, remote from said open outer end 14. The axial extent of the portion of the hollow cylindrical body 12 in which the first female thread 16 is located is relatively small, being long enough to accommodate approximately one turn of the first female thread 16.

Figure 3:
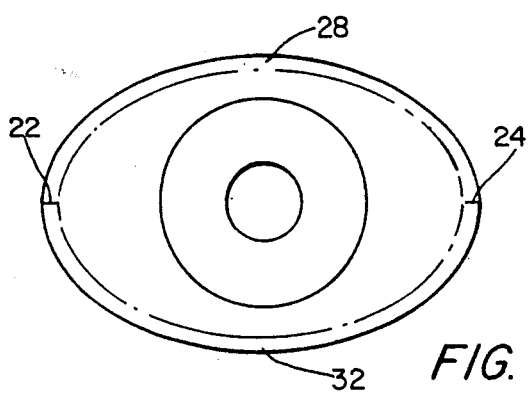
FIG. 3 is a view taken on the line 3—3 of FIG. 1.

An eyecup 20 extends from the hollow cylindrical body 12, flaring outwardly and being of generally elliptical shape, as shown in FIG. 3. The portions 22 and 24 of the lip of the eyecup 20 which are at the ends of the major axis of the generally elliptically shaped eyecup 20 extend further from the small end 26 of eyecup 20 than do the portions 28, 32 which are at the ends of the minor axis of the eyecup 20. Eyecup 20 at its upper, smaller end is generally cylindrical, so as to merge with the cylindrical body 12 opposite the open outer end 14 thereof. In the hollow body 12, opposite the outer end 14, there is a flange 34 having an opening 36 therethrough, and located centrally thereof. Further, at the juncture of the first threads 16 and the second threads 18, there is a shoulder 38.

Shown in FIG. 1 is a bottle B-1 of conventional construction, as is used for the dispensing of eyedrops. It is made of a suitable deformable plastic material, so that it may be squeezed, and is generally either cylindrical or elliptical in horizontal cross-section. The bottle B-1 has a neck 101. A nozzle 103 is seen extending axially beyond the end of the neck 101, having a duct 105 extending axially thereof. On the neck 101 of bottle B-1 is a male thread 107 which is in threaded engagement with the female thread 18 for approximately one turn, there being approximately two turns of the thread 107, as shown. The bottle B-1 has a shoulder 103a (see FIG. 4A) which engages the flange 36, which thereby serves as a stop.

When the bottle B-1 is squeezed, the liquid therein will flow from the duct 105 of nozzle 103 as discrete drops, and the eyecup 20 enables the liquid to flow from the applicator and into the eye of the person using the bottle B-1 and applicator attachment 10.

Figure 2:
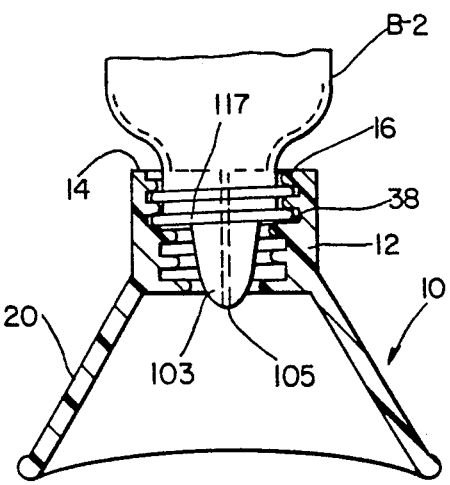
FIG. 2 is a view similar to FIG. 1, but having a large diameter neck bottle attached to it.

There is shown in FIG. 2 the eyedrop applicator attachment 10 having a bottle B-2 threaded into the hollow cylindrical body 12, and engaging the first female thread 16. The thread 117 of the bottle B-2 is of larger diameter than the thread 107 of the bottle B-1. The shoulder of the bottle B-2 engages the shoulder 38, which serves as a stop for the threading engagement of bottle B-2 with eyedrop applicator attachment 10. The nozzle 103 will be seen extending through the hollow cylindrical body 12, so that drops issuing from the duct 105 thereof will pass into the eye of the user, through the eyecup 20.

Figure 4:
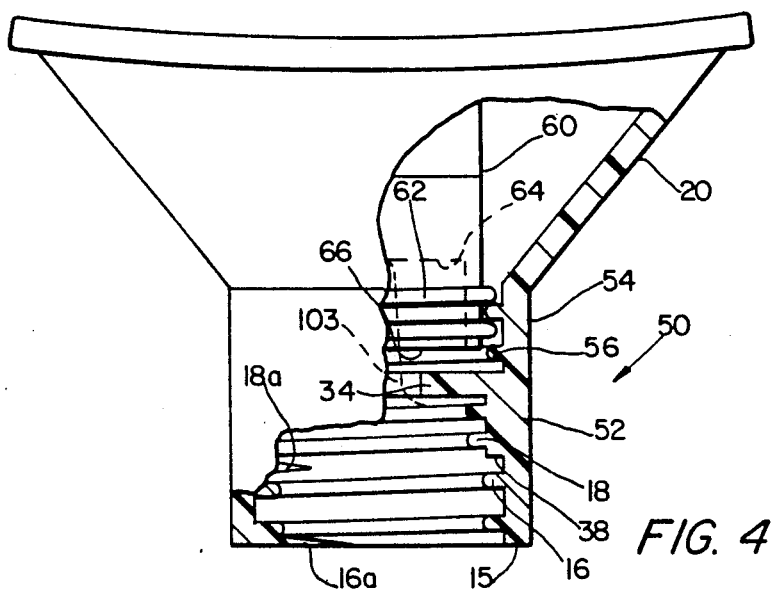
FIG. 4 is an elevational view, with parts in section, of an alternate embodiment of an eyedrop applicator attachment in accordance with the present invention, and including a stopper.

In FIG. 4, there is shown an attachment 50, which is different from the attachment 10 shown in FIGS. 1 and 2 in that there is provided a cylindrical hollow body 52 having a cylindrical extension 54 on the opposite side of the flange 34 from the threads 16 and 18, which is preferably the same exterior diameter as the body 52. The cylindrical extension 54 has a third female thread 56 therein, and a closure 60 has a male thread 62 thereon in engagement with the female thread 56. A nozzle 103 of a bottle is shown in phantom lines, nozzle 103 forming a part of either a bottle B-1 or B-2 which is engaged, respectively, with either the female thread 16 or the female thread 18. The stopper 62 is hollow, having an internal surface 64 located inwardly of the end 66 thereof. The surface 64 is at a depth slightly less than the extent of the shortest nozzle to be used with attachment 50. The stopper 60 will be seen to have been threaded into the attachment 50 until the surface 64 thereof has engaged with the end of the nozzle 103, to thereby seal the duct therein. If the bottle to which the attachment 50 has been attached has the tip of its nozzle 103 axially closer to the flange 34, the stopper 60 will be capable of being threaded further inwardly so that its end 66 approaches more closely the flange 34, and so that the surface 64 thereof can engage the tip of nozzle 103 and seal the duct therein.

Figure 4A:
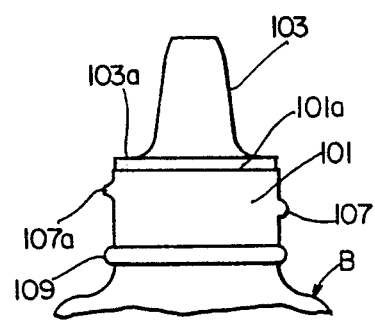
FIG. 4A is an elevational view of the upper portion of an eyedrop bottle.

Referring to FIG. 4A, there is shown the upper portion of a bottle B having a threaded neck 101 and nozzle 103. The thread 107 has its end 107a spaced from the end 101a of neck 101. The nozzle 103 will be seen to have a shoulder 103a: the distance from the end 107a of thread 107 to the shoulder 103a varies from 0.03 to 0.1 inches in different bottles. Further, the shortest distance on any production eyedropper bottle from the tamper-proof seal 109 to the shoulder 103a is 0.350 inches. The total axial length of the first female thread 16 and the second female thread 18 is, therefore, made to be this same distance. Allowing the required axial lengths for the threads 16 and 18, individually, and diminishing that length by the aforementioned distance between end 107a of thread 107 and shoulder 103a, there could result an insufficient engagement, of only about one-half turn, between the male threads on the bottle B: to provide for greater security, an engagement of the threads through almost a fill turn (approximately 324° of rotation) is achieved by causing the female thread 16 to be extended towards the end 15 of the cylindrical body 12. Thus, at the entry end 16a of the thread 16, the thread has been helically extended with its thickness reduced to approximately one-third of the normal thread thickness of 0.045 inches. Similarly, at the entry end 18a of thread 18 adjacent shoulder 38, thread 18 is helically extended with its thickness reduced.

Figure 5:
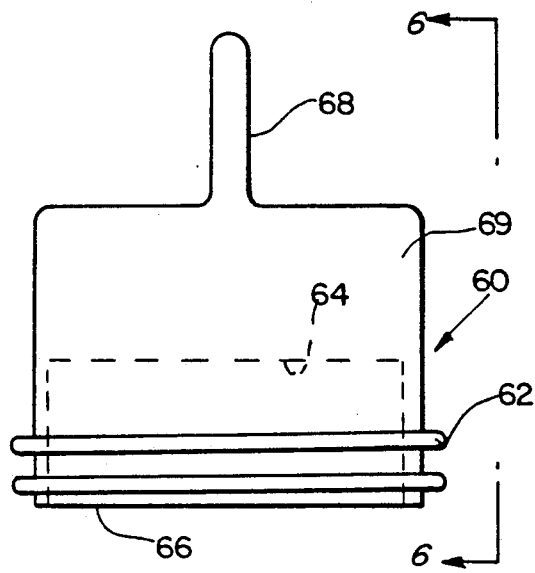
FIG. 5 is an elevational view of the stopper shown in FIG. 4.
Figure 6:
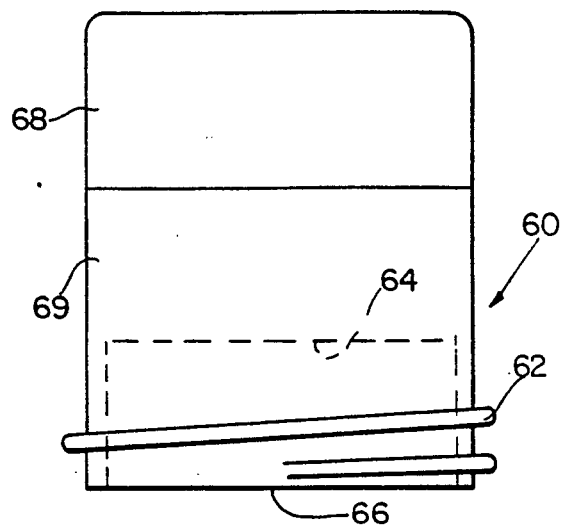
FIG. 6 is a view taken on the line 6—6 of FIG. 5.

The stopper 60 is shown in FIG. 5, and there may be seen the male thread 62 thereon, and the surface 64. The stopper 60 includes a finger-engaging portion 68 at its upper end, which is generally planar, and as shown in FIG. 6, extends substantially entirely across the generally lower cylindrical body portion 69.

Figure 7:
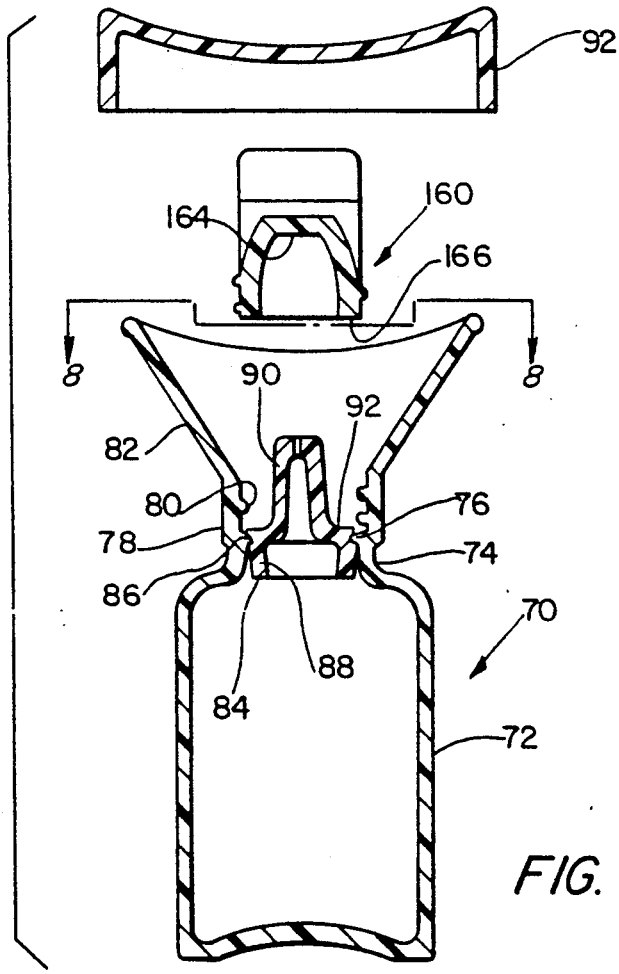
FIG. 7 is an exploded cross-sectional view of a combined bottle and eyecup in accordance with the present invention.
Figure 8:
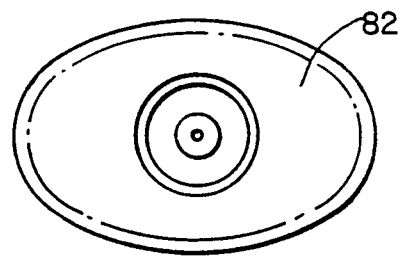
FIG. 8 is a view taken on the line 8—8 of FIG. 7.

A further embodiment of an eyedrop applicator in accordance with the present invention is shown in FIGS. 7 and 8, in which the applicator 70 includes a bottle 72 having a neck 74 with an internally directed flange 76. An extension 78 of the neck 74 has a female thread 80 within it and an eyecup 82 at its outer end. A nozzle insert 84 is provided having a groove 86 in a skirt portion 88, with a nozzle 90 extending upwardly from a shoulder 92 The insert 84 is assembled to the bottle 72 by the snap-fit engagement of flange 76 into groove 86. A stopper 160 is provided, generally similar to the stopper 60, but having a somewhat different configuration of the hollow portion thereof. The surface 164 of stopper 160 engages and seals the end of nozzle 90 when thread 162 thereof engages the thread 80, and the stopper 160 is turned down into extension 78. The end 166 engages the shoulder 92 in sealing relationship. In addition, there is provided a cap 92 for engaging with and closing off the open end of the eyecup 82.

Figure 9:
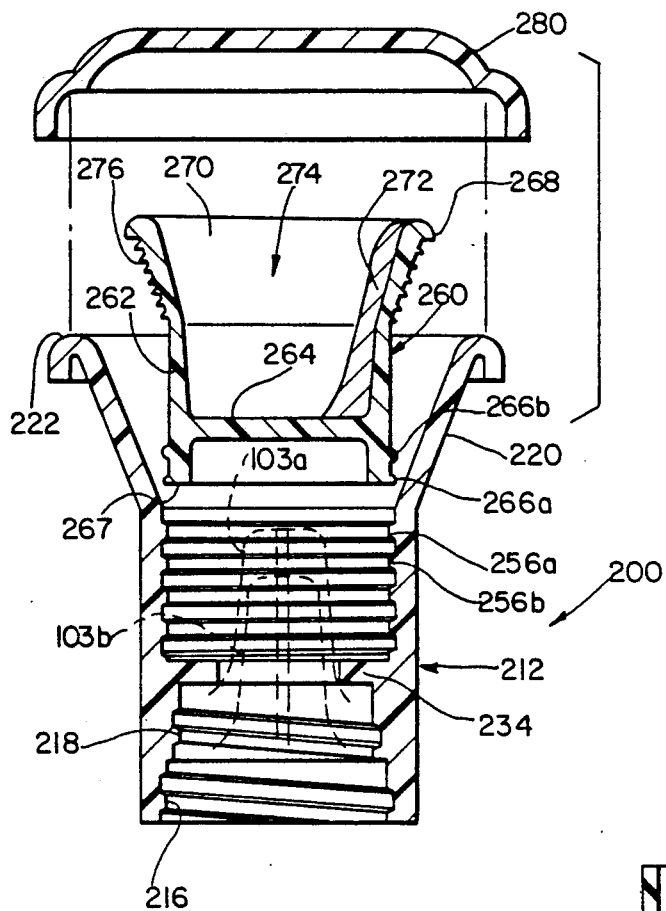
FIG. 9 is an exploded cross-sectional view of another embodiment of an eyedrop applicator in accordance with the present invention.

Another embodiment of an eyedrop applicator attachment in accordance with the present invention is shown in FIG. 9, wherein there is shown an eyedrop applicator attachment generally designated 200 and including a cylindrical body 212 having an integral eyecup 220, which is generally similar to the cylindrical body 52 shown in FIG. 4. The eyecup 220 flares outwardly like eyecup 230 and is positioned so that its narrow dimension is seen in this figure. There is provided in body 212 a double thread made up of a first thread 256a and a second thread 256b which have their termini spaced 180° from each other, and the turns of which are interspaced along the axis of cylindrical body 212. The stopper 260 is provided with mating double threads 266a and 266b. Although double threads have been illustrated, it will be apparent that other multiple threads may be provided, such as triple threads.

There is shown in phantom lines a nozzle 103a extending from a bottle having a Size No. 13 neck and therefore engaging with the second set of threads 218. There is also shown in phantom lines a nozzle 103b of a Size No. 15 bottle which will nave the threads thereof engaged with the larger diameter thread 216. As is apparent, the end of the nozzle 103a extends further into the body 212 than does the nozzle 103b. The stopper 260 has a transverse wall 264 which is spaced inwardly from the entry end 267 thereof. In order to cause the lower surface of the transverse wall 264 to engage and seal the duct within the nozzle 103a or the nozzle 103b, certain dimensional relationships are established. The axial length of the threads 256a and 256b on the interior wall of the cylindrical body 212 is approximately at least 0.4 inches, mace to accommodate the various lengths of the nozzles 103a and 103b. To permit engagement of the threads 266a and 266b on the stopper 260 with the threads 256a and 256b in the body 212, and to enable the engagement of the wall 264 with the end of the nozzle 103a or 103b, the distance from the bottom of the transverse wall 264 to the end 267 of stopper 260 is at most approximately 0.1 inches, and preferably is 0.11 inches.

Use of the above noted double male and double female threads on the stopper 260 and cylindrical body 212, respectively, insures uniform pressure and interference between the stopper 260 and the nozzle 103a or 103b, thereby insuring sealing of the duct on the nozzle 103a, 103b with only a half turn of the stopper 260. The plastic material of which the stopper 260 is made, as well as that of the hollow body 212 and the eyecup 220, is of a somewhat yielding nature, so that there is thereby obtained some compression of the transverse wall upon engagement with the nozzle 103 or 103b.

The stopper 260 will be seen to have a generally cylindrical body 262, although the upper portion 268 thereof may be outwardly flaring, having a rim 270 defining an open end, which is remote from the double thread 266a, 266b. The provision of a stopper having an open end safeguards against injury to the eye of a person who may forget to remove the stopper when attempting to dispense drops into the eye: there is no centrally disposed element to strike the eye. If the stopper 260 is not removed before attempting to dispense eyedrops from the bottle, only the rim 270 will strike the eye at a location remote from the sensitive cornea. A generally axially extending protrusion 272 extends inwardly into the well 274 provided by the open ended body 262 inwardly on rim 270: body 262 will be seen to be generally in the form of a thimble. A finger may be inserted into the non-cylindrical well 274, and by engaging the protrusion 272, cause rotation of the stopper 260. The well 274 will be seen to have, in effect, unequal major and minor transverse axes, which enable the well to serve as an internal finger gripping construction. In addition to the internal finger gripping construction provided by the protrusion 272, there is provided on the exterior surface of the body 262 knurling 276, to enable a person to rotate the stopper 260 by gripping it on this knurling and rotating it.

There is also shown in FIG. 9 a snap-fit lid 280 which is of substantially the size and of the generally elliptical eyecup 220, and which will engage the end 222 of eyecup 220, which will be seen to be rounded to avoid injury to a person using the attachment disclosed in FIG. 9.

Figure 10:
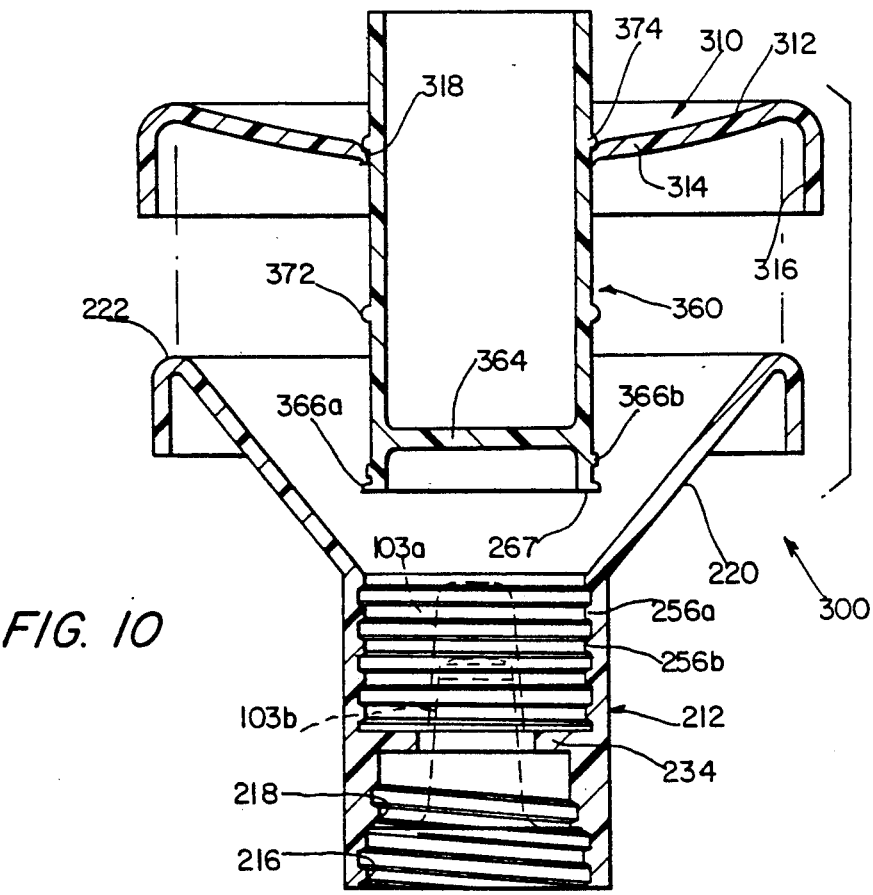
FIG. 10 is a cross-sectional view of still another embodiment of an eyedrop applicator in accordance with the present invention.

Referring now to FIG. 10, there is shown an eyedrop applicator attachment generally designated 300, and comprising a cylindrical body 212 and integral eyecup 220. The body 212 and eyecup 220 are shown rotated 90° from the position thereof shown in FIG. 9, so that the widest extent of eyecup 220 is shown. A combined stopper and lid 310 is provided, comprising a lid 312 having a plate 314 with a peripherally depending flange 316, and a central opening 318. As will be understood, the lid 312 is made of a suitable yielding plastic material, and is of the same size and shape as the end 222 of eyecup 220.

A stopper body 360 is provided, of generally hollow cylindrical configuration, and having a transverse wall 364 spaced from the adjacent entry end 367 thereof;

stopper body 360 has threads 366a and 366b for engagement with the threads 256a and 256b of the cylindrical body 212. Axially spaced on the exterior of stopper 360 are beads 372 and 374. Between the beads 372 and 374, the exterior of the stopper 360 is unobstructed and of the same or slightly smaller diameter than the opening 316, so that the stopper 360 can be slid lengthwise through and rotated on the opening 318. Thus, after a bottle has been fully engaged with the threads 216 or 218, the lid 310 is caused to snap-fit onto the end of the eyecup 220, and then the stopper 360 may be rotated to engage the threads 366a and 366b with the threads 256a and 256b, the rotation continuing to cause the lower surface of the transverse wall 364 to engage the nozzle 103 or 103b. The stopper shown in FIGS. 5, 9 and 10 may be used with the bottle 70 of FIG. 7.

There has been provided an eyedrop applicator attachment which is capable of being used interchangeably with any of the available eyedropper bottles now being produced, and which have been substantially standardized as to sizes. The attachment herein provided may be sold separately for use with available eyedrop medication bottles, and may be readily detached after exhaustion of one bottle, and attached to a replacement eyedrop medication bottle. The attachment herein provided may be made of readily available materials, and produced on conventional machinery, at low cost.

There is also provided an eyedrop applicator attachment with provision for a closure or stopper, so as to avoid leakage, which may be used with the attachment when it is attached with either of the commonly used sizes of eyedrop bottles, and ensure sealing engagement with the end of the nozzle thereof. Thus, there is provided a construction in which the attachment may be utilized with any of the currently produced eyedrop medication bottles, and which will enable sealing of the bottle and therefore permit the attachment to remain in place until the contents of the bottle have been exhausted.

There has been provided herein a combined bottle for eyedrop medication, a drop-forming nozzle and eyecup, with closure and cap, all constructed to provide for both retention of the eyedrop medication against evaporation during periods of non-use, against contamination, and against the entry of foreign matters into the eyecup.

The claims and the specification describe the invention presented, and the terms that are employed in the claims draw their meaning from the use of such terms in the specification. Some terms employed in the prior art may be broader in meaning than specifically employed herein. Whenever there is a question between the broader definition of such term as used in the prior art and the more specific use of the term herein, the more specific meaning is meant.

What is claimed is:

1. An eyedrop applicator attachment for a bottle having a drop forming nozzle extending beyond male threads on the bottle comprising:
   (a) a cylindrical body having means thereon for engaging either a relatively large or relatively small diameter thread on a bottle having either a relatively large or a relatively small neck, and
   (b) an eyecup diverging outwardly and axially from said cylindrical body adjacent said second thread means, and having an edge remote from said cylindrical body,
   said cylindrical body having second female thread means therein axially of said first mentioned thread means for engaging a male thread, and in combination therewith, a stopper having external thread means for engaging said second female thread means.

2. An eyedrop applicator attachment for a bottle with an externally threaded neck,
   the attachment comprising:
   a hollow cylindrical body with an open outer end for entry thereinto of the neck of a bottle,
   a first female thread on the interior of said body adjacent the open outer end thereof,
   a second female thread of smaller diameter than said first thread on the interior of said body axially of said first female thread and remote from said open outer end, and
   means for enabling liquid to flow from said applicator when the neck of the bottle is threadedly engaged with one said female thread,
   a flange in said body at the inner end of said second thread, an aperture in said flange, a third female thread in said body inwardly of said flange and axially between said flange and said liquid flow enabling means,
   whereby said eyedrop applicator attachment may be attached either to a bottle having a neck with an external thread having a size to engage said first thread or to a bottle having a neck with external thread having a size to engage said second female thread,
   and a stopper having a male thread engaging said third female thread.

3. An eyedrop applicator attachment for a bottle with an externally threaded neck,
   the attachment comprising:
   a hollow cylindrical body with an open outer end for entry thereinto of the neck of a bottle,
   a first female thread on the interior of said body adjacent the open outer end thereof,
   a second female thread of smaller diameter than said first thread on the interior of said body axially of said first female thread and remote from said open outer end, and
   means for enabling liquid to flow from said applicator when the neck of the bottle is threadedly engaged with one said female thread,
   a flange in said body at the inner end of said second thread, an aperture in said flange, a third female thread in said body inwardly of said flange and axially between said flange and said liquid flow enabling means,
   whereby said eyedrop applicator attachment may be attached either to a bottle having a neck with an external thread having a size to engage said first thread or to a bottle having a neck with external thread having a size to engage said second female thread,
   and a stopper having a male thread engaging said third female thread,
   said stopper comprising means for engaging said flange.

4. An eyedrop applicator attachment for a bottle with an externally threaded neck,
   the attachment comprising:
   a hollow cylindrical body with an open outer end for entry thereinto of the neck of a bottle, a first female thread on the interior of said body adjacent the open outer end thereof, a second female thread of smaller diameter than said first thread on the interior of said body axially of said first female thread and remote from said open outer end, and means for enabling liquid to flow from said applicator when the neck of the bottle is threadedly engaged with one said female thread, a flange in said body at the inner end of said second thread, an aperture in said flange, a third female thread in said body inwardly of said flange and axially between said flange and said liquid flow enabling means, whereby said eyedrop applicator attachment may be attached either to a bottle having a neck with an external thread having a size to engage said first thread or to a bottle having a neck with external thread having a size to engage said second female thread, and a stopper having a male thread engaging said third female thread, said stopper comprising means for engaging and sealing the dropper of a bottle when said attachment is threaded onto a bottle.

* * * * *